US010045918B2

(12) United States Patent
Gershon et al.

(10) Patent No.: US 10,045,918 B2
(45) Date of Patent: Aug. 14, 2018

(54) EMBEDDING OXIDE PARTICLES WITHIN SEPARATE PARTICLES FOR SUNSCREEN APPLICATIONS

(71) Applicant: International Business Machines Corporation, Armonk, NY (US)

(72) Inventors: Talia S. Gershon, White Plains, NY (US); Yun Seog Lee, Yorktown Heights, NY (US); Ning Li, White Plains, NY (US); Devendra Sadana, Pleasantville, NY (US); Teodor K. Todorov, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/142,797

(22) Filed: Apr. 29, 2016

(65) Prior Publication Data

US 2017/0112731 A1    Apr. 27, 2017

Related U.S. Application Data

(60) Provisional application No. 62/245,250, filed on Oct. 22, 2015.

(51) Int. Cl.
| *A61K 8/25* | (2006.01) |
| *A61K 8/02* | (2006.01) |
| *A61K 8/11* | (2006.01) |
| *A61Q 17/04* | (2006.01) |
| *A61K 8/27* | (2006.01) |

(52) U.S. Cl.
CPC .............. *A61K 8/11* (2013.01); *A61K 8/25* (2013.01); *A61K 8/27* (2013.01); *A61Q 17/04* (2013.01); *A61K 2800/26* (2013.01); *A61K 2800/412* (2013.01); *A61K 2800/413* (2013.01); *A61K 2800/651* (2013.01); *A61K 2800/805* (2013.01)

(58) Field of Classification Search
CPC .................... A61K 8/25; A61Q 17/04
See application file for complete search history.

(56) References Cited

U.S. PATENT DOCUMENTS

| 3,761,261 | A  | 9/1973  | Ono et al. |
| 3,863,007 | A  | 1/1975  | Warner, Jr. |
| 4,549,195 | A  | 10/1985 | Bluzer |
| 5,011,782 | A  | 4/1991  | Lamb |
| 5,147,125 | A  | 9/1992  | Austin |
| 5,223,250 | A  | 6/1993  | Mitchell |
| 5,441,726 | A  | 8/1995  | Mitchnick |
| 5,534,056 | A  | 7/1996  | Kuehnle |
| 5,902,569 | A  | 5/1999  | Oshima |
| 6,419,909 | B1 | 7/2002  | Lorant |
| 7,241,399 | B2 | 7/2007  | Haubold |
| 9,056,063 | B2 | 6/2015  | Hanson |
| 9,144,535 | B1 | 9/2015  | Daly et al. |
| 9,144,536 | B1 | 9/2015  | Daly et al. |
| 9,773,931 | B2 | 9/2017  | Hossain et al. |
| 2002/0122832 | A1 | 9/2002  | Hanke |
| 2003/0102099 | A1 | 6/2003  | Yadav |
| 2004/0209081 | A1 | 10/2004 | Hagihara |
| 2005/0008861 | A1 | 1/2005  | Yadav et al. |
| 2005/0048010 | A1 | 3/2005  | Kliss |
| 2005/0208005 | A1 | 9/2005  | Giroud |
| 2005/0227063 | A1 | 10/2005 | Lawandy |
| 2005/0238600 | A1 | 10/2005 | Lien |
| 2005/0265935 | A1 | 12/2005 | Hollingsworth |
| 2006/0228310 | A1 | 10/2006 | Lyth |
| 2006/0270053 | A1 | 11/2006 | Tilak |
| 2007/0280895 | A1 | 12/2007 | Weimer |
| 2008/0149850 | A1 | 6/2008  | Tardif et al. |
| 2008/0220026 | A1 | 9/2008  | Maltra |
| 2009/0022765 | A1 | 1/2009  | Chung et al. |
| 2009/0104130 | A1 | 4/2009  | Bernstein |
| 2009/0258072 | A1 | 10/2009 | Schlossman |
| 2009/0258230 | A1 | 10/2009 | Schlossman |
| 2010/0008872 | A1 | 1/2010  | Katusic |
| 2010/0055138 | A1 | 3/2010  | Margulies |
| 2011/0268678 | A1 | 11/2011 | Armstrong |
| 2013/0216834 | A1 | 8/2013  | Hashimoto |
| 2014/0142213 | A1 | 5/2014  | Weiss |
| 2015/0283059 | A1 | 10/2015 | Nagare |
| 2016/0082513 | A1 | 3/2016  | Niedermeyer |

FOREIGN PATENT DOCUMENTS

| CN | 103071535 A    | 5/2013  |         |
| EP |    1889810 A1 * | 2/2008  | ............. A01N 59/16 |
| JP |   09059591 A    | 3/1997  |         |
| JP | 2008024677 A    | 2/2008  |         |
| JP | 2011102291 A    | 5/2011  |         |
| WO | 2005023535 A2   | 3/2005  |         |
| WO | 2008017176 A2   | 2/2008  |         |
| WO | 2008079758 A1   | 7/2008  |         |
| WO | 2011004133 A2   | 1/2011  |         |
| WO | 2012046204 A1   | 4/2012  |         |
| WO | 2013040149      | 3/2013  |         |
| WO | 2013094639 A1   | 6/2013  |         |
| WO | 2014049139 A1   | 4/2014  |         |
| WO | 2014077189      | 5/2014  |         |
| WO | 2016020168 A1   | 2/2016  |         |

OTHER PUBLICATIONS

Faure, B. et al. "Dispersion and surface functionalization of oxide nanoparticles for transparent photocatalytic and UV-protecting coatings and sunscreens", Sci Technol. Adv. Mater. 14 2013, 023001.*

(Continued)

*Primary Examiner* — Gina C Justice
(74) *Attorney, Agent, or Firm* — Ryan, Mason & Lewis, LLP

(57) ABSTRACT

Zinc oxide compositions and methods for embedding oxide particles in a separate suspension particle for sunscreen applications are provided herein. A method includes reducing the size of each of multiple zinc oxide particles in accordance with a predetermined range; selecting one or more suspension particles to be utilized in conjunction with the multiple zinc oxide particles in a sunscreen composition, wherein each of the one or more suspension particles is larger in size than each of the multiple zinc oxide particles, and wherein said selecting is based on the refractive index of each of the one or more suspension particles; and embedding the multiple zinc oxide particles into the one or more suspension particles to create the sunscreen composition.

10 Claims, 1 Drawing Sheet

(56) References Cited

OTHER PUBLICATIONS

Thokozane Moses Sithole, Synthesis and characterization of MBxOy:Eu (M=Ca, Sr, Ba) phosphors and TiO2 semiconductor for application in luminescence and energy materials, University of the Free State, Nov. 2014.

Sardar et al., Optical-absorption intensities and intermanifold emission cross sections of trivalent erbium ions in calcium fluorophosphate, Journal of Applied Physics, Sep. 2005.

Lu et al., 2008—White Up-Conversion Luminescence in Rare-Earth-Ion-Doped YAIO3 Nanocrystals, J. Phys. Chem. C 2008, 112, 15071-15074.

Refractive index of ZnO (Zinc oxide)—Bond-o, http://refractiveindex.info/?shelf=main&book=ZnO&page=Bond-o, Mar. 25, 2016.

Refractive index of SiO2 (Silicon dioxide, Silica, Quartz)—Malitson, http://refractiveindex.info/?shelf=main&book=SiO2&page=Malitson, Mar. 25, 2016.

Schubert et al., Design of multilayer antireflection coatings made from co-sputtered and low-refractive-index materials by genetic algorithm. Optics Express vol. 16, No. 8, 2008.

Law et al., ZnO—Al2O3 and ZnO—TiO2 Core-Shell Nanowire Dye-Sensitized Solar Cells. J. Phys. Chem. B 2006, 110, 22652-22663.

Pu et al., Core/shell structured ZnO/SiO2 nanoparticles: Preparation, characterization and photocatalytic property. Applied Surface Science 257 (2010) 393-397.

Mantz et al., Progress in Organic Coatings 47 (2003) 432-442, "A multiple-scattering model analysis of zinc oxide pigment for spacecraft thermal control coatings."

Song et al., Toxicology Letters 199 (2010) 389-397, "Role of the dissolved zinc io and reactive oxygen species in cytotoxicity of ZnO nanoparticles."

Bohren et al., "Absorption and Scattering of Light by Small Particles", Wiley-VCH, © 2004, Weinheim.

Bae et al., J. Phys. Chem. B 2005, 109, 2526-2531, "Comparative Structure and Optical Properties of Ga-, In-, and Sn-Doped ZnO Nanowires Synthesized by thermal evaporation."

NanoComposix, Silver Nanoparticles: Optical Properties, http://nanocomposix.com/pages/silver-nanoparticles-optical-properties, Apr. 20, 2016.

Awazu et al., 2007—A Plasmonic Photocatalyst Consisting of Silver Nanoparticles Embedded in Titanium Dioxide, J. Am. Chem. Soc. 2008, 130, 1676-1680.

Sherry et al., Localized Surface Plasmon Resonance Spectroscopy of Single Silver Nanocubes, Nano Lett., vol. 5, No. 10, 2005.

Aguirre et al., Ag@ZnO Core_Shell Nanoparticles Formed by the Timely Reduction of Ag+ Ions and Zinc Acetate Hydrolysis in N,N-Dimethylformamide: Mechanism of Growth and Photocatalytic Properties, J. Phys. Chem. C 2011, 115, 24967-24974.

Haynes et al., Nanosphere Lithography: Tunable Localized Surface Plasmon Resonance Spectra of Silver Nanoparticles, J. Phys. Chem. B 2000, 104, 10549-10556.

J. Nobbmann, "FAQ: How important are refractive index & adsorption for nanoparticles?" http://www.materials-talks.com/blog/2014/08/05/faq-how-important-are-refractive-index-absorption-for-nanoparticles/ Materials Talks, Aug. 5, 2014, p. 1-2.

Tsuzuki et al., Nanoparticle Coatings for UV Protective Textiles, RJTA vol. 14 No. 2 2010.

Li et al., Transparent and Light-Emitting Epoxy Super-Nanocomposites Containing ZnO-QDs/SiO2 Nanocomposite Particles as Encapsulating Materials for Solid-State Lighting, J. Phys. Chem. C 2008, 112, 18616-18622.

Li et al., 2011—Sol-gel preparation and characterization of nanoporous ZnO_SiO2 coatings with broadband antireflection properties, Applied Surface Science 257 (2011) 9752-9756.

Messaoudi et al., "Synthesis and characterization of ZnO/Cu2O core-shell nanowires grown by two-step electrodeposition method." Applied Surface Science 343 (2015) 148-152.

Luo et al., Facile synthesis of composition-tuned ZnO/ZnxCd1-xSe nanowires for photovoltaic applications, Nanoscale Research Letters (2015) 10:181.

Ultraviolet Radiation and the INTERSUN Programme [online]. WHO, Nov. 2003 [retrieved on Jun. 8, 2017]. Retrieved from the internet <http://www.who.int/uv/uv_and_health/en/>.

Smijs et al. Titanium Dioxide and Zinc Oxide Nanoparticles in Sunscreens: Focus on Their Safety and Effectiveness, Nanotechnology, Science and Applications 4:95-112, Oct. 2011.

Wikipedia, List of Refractive Indices, last modified Feb. 15, 2017; https://en.wikipedia.org/wiki/List_of_refractive_indices.

Naylor et al. "Sunscreens," accessed 2017, http://telemedicine.org/sundam/sundam2.4.2.html.

Cuprous Oxide, Chemical Book, pp. 1-4, Accessed Sep. 18, 2017, https://www.chemicalbook.com/ProductChemicalPropertiesCB9853041_EN.htm.

Tariq Jan, et al. Sn Doping Induced Enhancement in the Activity of ZnO Nanostructures Against Antibiotic Resistant S. aureus Bacteria; Int J. Nanomedicine, vol. 8, pp. 3679-3687; Published online Sep. 30, 2013.

Bhatti et al. Optical Properties of Chromium & Cobalt Doped Zinc Oxide Powder Prepared by Sol-Gel Combustion Method, with the Assistance of Microwave Radiations; International Journal of Advanced Tech. in Engineering and Science; vol. 3, Issue 10; pp. 80-85; published Oct. 2015.

Machine translation WO 2011/004133, printed 2017.

Wikipedia "Band Gap" last modified Jul. 18, 2017, https://en.wikipedia.org/wiki/Band_gap.

Machine translation WO 2012/046204, printed 2017.

Family Health Team, "Best Ways to Protect Your Hair From Sun Damage," Cleveland Clinic, health essentials, <https://health.clevelandclinic.org/2014/08/best-ways-to-protect-your-hair-from-sun-damage/>, published Aug. 22, 2014, p. 1-4.

Simon Aldridge and Anthony Downs. The Group 13 Metals Aluminum, Gallium, Indium and Thallium Chemical Patterns and Peculiarities, 2011 John Wiley & Sons, Ltd., p. 623 (Year: 2011).

Machine translation, JP 2008-024677, printer 2018.

Kelly et al. "The Optical Properties of Metal Nanoparticles: The Influence of Size, Shape and Dielectric Environment," Journal of Physical Chemistry B 107:668-677, 2003.

Garcia, "Surface Plasmons in Metallic Nanoparticles: Fundamentals and Applications," Journal of Physics D: Applied Physics 44(28), 283001, 2011.

English language translation of WO 2013 094639 (A1) (Year: 2013).

\* cited by examiner

EMBEDDING OXIDE PARTICLES WITHIN SEPARATE PARTICLES FOR SUNSCREEN APPLICATIONS

FIELD

The present application generally relates to chemical technology, and, more particularly, to sunscreen technologies.

BACKGROUND

Sunscreen creams and other such compositions are commonly used to prevent ultraviolet (UV) radiation (also referred to herein as "light" in this context) from reaching the skin of a human user and causing damage. It is noted that UV light is an electromagnetic radiation with a wavelength range between approximately 280 nanometers (nm) and approximately 400 nanometers (specifically, that is the range of UV radiation that is not absorbed by the ozone).

A common active ingredient of existing sunscreen compositions is zinc oxide (ZnO). ZnO is a semiconductor that has a specific band gap, and particles of ZnO used in existing sunscreen compositions are typically approximately 50-200 nm in size. Additionally, in existing sunscreen compositions, typical ZnO materials are capable of absorbing UV light (that is, blocking the UV light from passing through the sunscreen composition to be absorbed by the skin of the user) within a wavelength range of approximately 290 nm through only approximately 350-380 nm.

Additionally, high sun protection factor (SPF) sunscreen compositions, which can absorb a large majority of the UV light in the range of 290-380 nm, require the addition of a higher density of ZnO particles, which causes the composition to become white and/or opaque due to light scattering from the ZnO particles, and which is an often undesirable property to consumers.

SUMMARY

In one embodiment of the present invention, zinc oxide compositions and methods for embedding oxide particles in a separate particle for sunscreen applications are provided. An exemplary method can include reducing the size of each of multiple zinc oxide particles in accordance with a predetermined range; selecting one or more suspension particles to be utilized in conjunction with the multiple zinc oxide particles in a sunscreen composition, wherein each of the one or more suspension particles is larger in size than each of the multiple zinc oxide particles, and wherein said selecting is based on the refractive index of each of the one or more suspension particles; and embedding the multiple zinc oxide particles into the one or more suspension particles to create the sunscreen composition.

In another embodiment of the invention, a sunscreen composition can include one or more suspension particles selected based the refractive index of each of the one or more suspension particles; and multiple zinc oxide particles embedded into the one or more suspension particles to create a sunscreen composition, wherein each of the multiple zinc oxide particles comprise a size of less than 200 nanometers, and wherein each of the one or more suspension particles is larger in size than each of the multiple zinc oxide particles.

These and other objects, features and advantages of the present invention will become apparent from the following detailed description of illustrative embodiments thereof, which is to be read in connection with the accompanying drawings.

DETAILED DESCRIPTION

As described herein, an embodiment of the present invention includes zinc oxide compositions, methods of fabrications thereof and methods of use thereof. Specifically, at least one embodiment of the invention includes embedding oxide particles within separate particles for sunscreen applications. As also detailed herein, in one or more embodiments of the invention, the encapsulating particles can be comprised of any material that has a sufficiently large band gap (greater than approximately 3.2 electron volts (eV), for example) and a refractive index between that of air and ZnO. One example, as noted herein, of such a material can include $SiO_2$.

As further detailed herein, one or more embodiments of the invention include generating ZnO compositions and methods of use thereof for effectively blocking more and/or all of the complete spectrum of UV light (that is, as noted above, the UV radiation that is not absorbed by the ozone, and which ranges between approximately 280 nm and 400 nm) while also preventing whitening effects caused by the scattering of light in the visible spectrum (that is, radiation between approximately 400 nm and 700 nm). As used herein, "scattering" refers to the deflection of rays of visible light from their original path due to interaction with particle surfaces.

Figure 1:
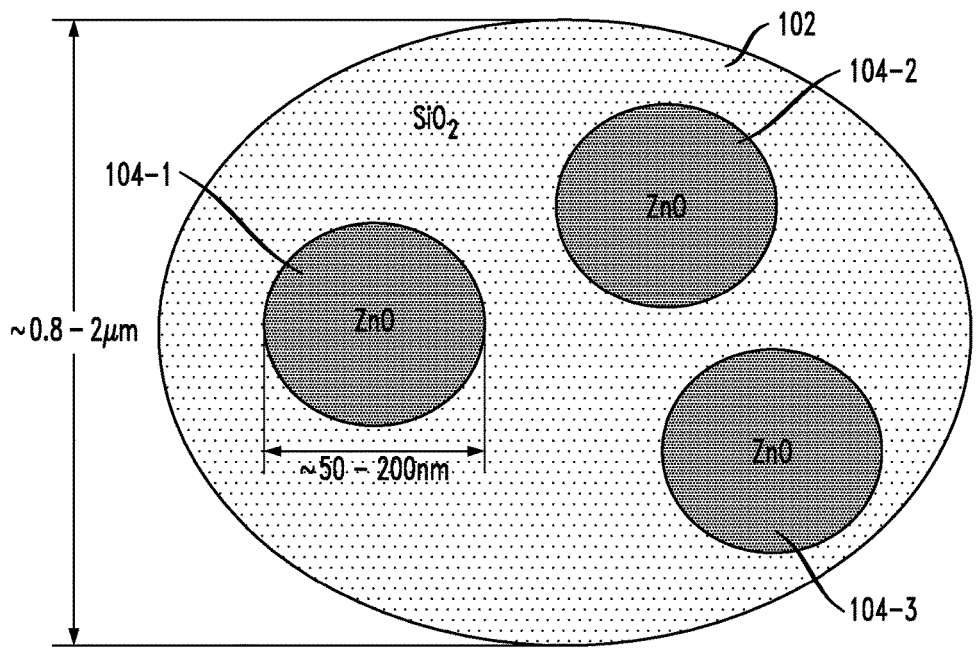
FIG. 1 is a diagram illustrating ZnO particles embedded within a silicon dioxide ($SiO_2$) particle, according to an exemplary embodiment of the invention.
Figure 2:
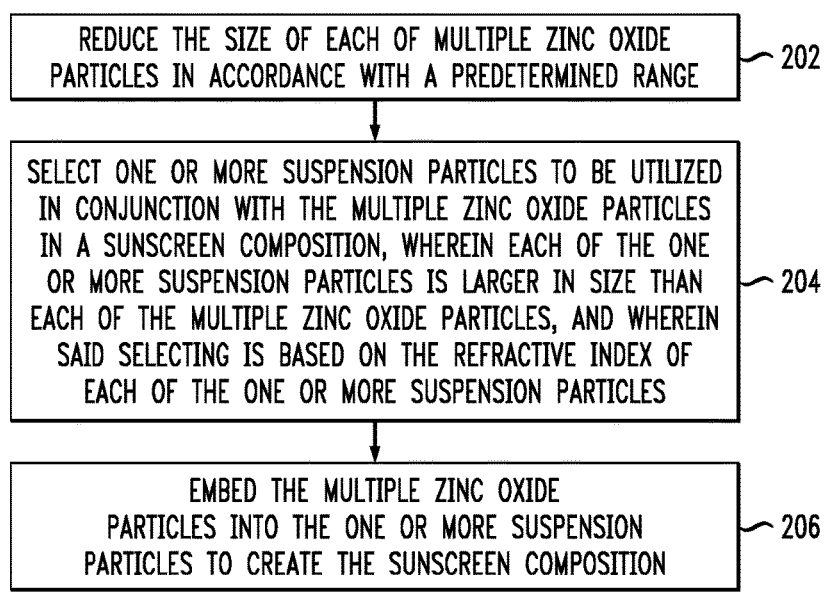
FIG. 2 is a flow diagram illustrating techniques, according to an embodiment of the invention.

FIG. 1 is a diagram illustrating ZnO particles embedded within an $SiO_2$ particle, according to an exemplary embodiment of the invention. By way of illustration, FIG. 1 depicts ZnO particles 104-1, 104-2 and 104-3 (collectively, 104) embedded within an $SiO_2$ particle 102. In one or more embodiments of the invention (such as the example embodiment depicted in FIG. 1), the size of each individual ZnO particle 104 is reduced (for use in a sunscreen composition) to less than 200 nm. By way of example, at least one embodiment of the invention includes reducing the size of each ZnO particle to a size of between approximately 50 and 100 nm.

Such reduction in particle size can reduce scattering from visible light. It is to be appreciated that particles well-described by Mie theory have a scattering "resonance," also referred to as a wavelength of light that the particle scatters most effectively. The position of the resonance relates to the manner in which light interacts with the particle. Scattering is sometimes described as a transfer of the electromagnetic radiation from the photons to the collective electrons in the particle, and then the transferring of that energy back into the scattered photon. Having a larger particle changes this process, and the result is a change in the resonance of the Mie scattering. Also, it is noted that Mie scattering is strong when particle size is approximately the same as visible light. Further, the extinction cross-section, $C_{ext}$, is reduced as particle size decreases. The extinction cross-section, $C_{ext}$, is a value that represents how effective a particle is at attenuating light. Generally, smaller particles have a lower $C_{ext}$ than do larger particles.

Accordingly, one or more embodiments of the invention include embedding one or more ZnO particles that have been reduced in size inside of a larger carrier and/or suspension particle (such as, for example, a $SiO_2$ particle that is on the order of 0.8-2 micrometers in size). The larger carrier particle provides safety benefits, due, for instance, to the fact that particles of this size cannot penetrate skin. This allows smaller ZnO particles to be used (embedded therein), which provides an optical benefit while still preventing potentially-harmful penetration of the small particles into the skin. Such embedding and/or suspending of the reduced-size ZnO particles within a (larger) silicon dioxide ($SiO_2$) shell and/or particle is in FIG. 1. By way of example, an $SiO_2$ particle utilized in one or more embodiments of the invention can be of a size that is between 0.8 and 2 micrometers.

FIG. 2 is a flow diagram illustrating techniques, according to an embodiment of the present invention. Step 202 includes reducing the size of each of multiple zinc oxide particles in accordance with a predetermined range. In at least one embodiment of the invention, the predetermined range can include less than 200 nanometers. Additionally, in at least one embodiment of the invention, the predetermined range can include between 50 and 100 nanometers.

Step 204 includes selecting one or more suspension particles to be utilized in conjunction with the multiple zinc oxide particles in a sunscreen composition, wherein each of the one or more suspension particles is larger in size than each of the multiple zinc oxide particles, and wherein said selecting is based on the refractive index of each of the one or more suspension particles. In at least one embodiment of the invention, the refractive index of each of the one or more suspension particles is between that of air and zinc oxide.

Also, in one or more embodiments of the invention, the one or more suspension particles can include one or more silicon dioxide particles. Additionally, in at least one embodiment of the invention, each of the one or more suspension particles can include a size of between 0.8 and 2 micrometers.

The selecting step can be further based, for example, on one or more optical properties of each of the one or more suspension particles. The one or more optical properties can include the band gap of each of the one or more suspension particles. By way of example, in one or more embodiments of the invention, the band gap of each of the one or more suspension particles comprises approximately 3.2 electron volts. Additionally, the one or more optical properties can include an amount of reduction of the scattering efficiency of each of the multiple zinc oxide particles imparted by each of the one or more suspension particles.

Step 206 includes embedding the multiple zinc oxide particles into the one or more suspension particles to create the sunscreen composition.

Also, an additional embodiment of the invention includes a sunscreen composition that includes one or more suspension particles selected based the refractive index of each of the one or more suspension particles, and multiple zinc oxide particles embedded into the one or more suspension particles to create a sunscreen composition, wherein each of the multiple zinc oxide particles comprise a size of less than 200 nanometers, and wherein each of the one or more suspension particles is larger in size than each of the multiple zinc oxide particles.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of another feature, step, operation, element, component, and/or group thereof.

At least one embodiment of the present invention may provide a beneficial effect such as, for example, improving the safety of sunscreen compositions based on reduced-size ZnO particles by embedding multiple such ZnO particles in a larger $SiO_2$ particle.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, comprising:

reducing the size of each of multiple zinc oxide particles to between 150 nanometers and 200 nanometers;

selecting one or more suspension particles to be utilized in conjunction with the multiple zinc oxide particles in a sunscreen composition, wherein each of the one or more suspension particles is a size of between 1.5 micrometers and 2 micrometers, and wherein said selecting is based on the refractive index of each of the one or more suspension particles; and embedding two or more of the zinc oxide particles into each of the one or more suspension particles to create the sunscreen composition.

2. The method of claim 1, wherein the one or more suspension particles comprise one or more silicon dioxide particles.

3. The method of claim 1, wherein the refractive index of each of the one or more suspension particles is between that of air and zinc oxide.

4. The method of claim 1, wherein said selecting is further based on one or more optical properties of each of the one or more suspension particles.

5. The method of claim 4, wherein the one or more optical properties comprises the band gap of each of the one or more suspension particles.

6. The method of claim 5, wherein the band gap of each of the one or more suspension particles comprises approximately 3.2 electron volts.

7. The method of claim 4, wherein the one or more optical properties comprises an amount of reduction of the scattering efficiency of each of the multiple zinc oxide particles imparted by each of the one or more suspension particles.

8. A sunscreen composition comprising:

one or more suspension particles selected based the refractive index of each of the one or more suspension particles, wherein each of the suspension particles is of a size of between 1.5 micrometers and 2 micrometers, and wherein the band gap of each of the one or more suspension particles comprises approximately 3.2 electron volts; and multiple zinc oxide particles embedded into each of the one or more suspension particles, wherein each of the multiple zinc oxide particles is a size of between 150 nanometers and 200 nanometers.

9. The composition of claim 8, wherein the one or more suspension particles comprise one or more silicon dioxide particles.

10. The composition of claim 8, wherein the refractive index of each of the one or more suspension particles is between that of air and zinc oxide.

* * * * *